(12) United States Patent
Bove (10) Patent No.: US 7,931,577 B2
(45) Date of Patent: Apr. 26, 2011

(54) MAGNETIC FIELD APPLICATOR SYSTEM

(75) Inventor: Thomas Bove, Greenacres, WA (US)

(73) Assignee: Tab Licensing Company, LLC, Port Jefferson, NY (US)

( * ) Notice: Subject to any disclaimer, the term of this patent is extended or adjusted under 35 U.S.C. 154(b) by 1263 days.

(21) Appl. No.: 11/344,742

(22) Filed: Jan. 31, 2006

(65) Prior Publication Data

US 2007/0179333 A1    Aug. 2, 2007

(51) Int. Cl.
*A61N 2/06* (2006.01)
*A61N 2/08* (2006.01)

(52) U.S. Cl. .............................................. 600/15; 600/9

(58) Field of Classification Search ................ 600/9–15; 29/898; 335/301, 303; 425/78
See application file for complete search history.

(56) References Cited

U.S. PATENT DOCUMENTS

| | | | | |
|---|---|---|---|---|
| 178,611 A | * | 6/1876 | Dye .............................. | 607/149 |
| 3,206,657 A | * | 9/1965 | Moriya .......................... | 335/303 |
| 3,921,620 A | * | 11/1975 | Nakayama ...................... | 600/15 |
| 4,489,711 A | * | 12/1984 | Latzke ............................. | 600/15 |
| 4,758,813 A | * | 7/1988 | Holsinger et al. ............. | 335/306 |
| 4,764,743 A | * | 8/1988 | Leupold et al. ................ | 335/306 |
| 4,910,057 A | * | 3/1990 | Ide et al. ....................... | 428/36.9 |
| 5,195,335 A | * | 3/1993 | Hart ................................. | 63/3.2 |
| 5,486,802 A | * | 1/1996 | Leupold ........................ | 335/306 |
| 5,538,495 A | * | 7/1996 | Ardizzone ........................ | 600/9 |
| 6,537,196 B1 | * | 3/2003 | Creighton et al. .............. | 600/12 |
| 6,796,937 B1 | * | 9/2004 | Bates .............................. | 600/15 |

FOREIGN PATENT DOCUMENTS

WO    WO 03006102 A2 *    1/2003

* cited by examiner

*Primary Examiner* — Charles A Marmor, II
*Assistant Examiner* — Catherine E. Burk
(74) *Attorney, Agent, or Firm* — Wells St. John PS

(57) ABSTRACT

A magnetic field applicator system wherein a plurality of magnets are generally fixed within an applicator base, each of the plurality of magnets having a magnetic axis at an angle different to other magnets in the plurality of magnets. The magnetic axis may be random with respect to others within the plurality of magnets. Also disclosed is a system for making the magnetic field applicator system.

25 Claims, 11 Drawing Sheets

FIG. 9

MAGNETIC FIELD APPLICATOR SYSTEM

TECHNICAL FIELD

This invention pertains to a magnetic field applicator system, mote particularly method for making a magnetism applicator and the applicator wherein the magnetic axis of individual magnets are at varying angles or orientations.

BACKGROUND OF THE INVENTION

The therapeutic, healing, preventative, health effect and biological effects of the application of numerous types and magnitudes of magnetic and/or electro-magnetic fields have been studied and are the subject of numerous articles, studies, testimonials, and prior patents, such as U.S. Pat. Nos. 5,084,003, 3,921,620, 5,002,068 (each of which are incorporated herein by reference). Exposing part or all of the human body to certain magnetic fields may accomplish any one of a number of different therapeutic effects such as: muscular and nerve pain alleviation; diabetic neuropathy; arthritis; improved healing; an increase in the circulation of the blood in the area in which the magnetic field and/or magnetic flux for instance are imposed; and others. While there are many different and overlapping theories on why it works, it is believed that the differential or torque created by a magnetic flux the induces voltage differentials and stimulates the body.

In prior applicator systems for applying magnetism or magnetic fields, the magnets or magnetic material is magnetized and maintained in an arrangement such that the magnetic axis is perpendicular to the applicator or application surface, such that prior art devices direct magnetic flux in one predominant direction relative to the surface of the applicator. Bar shaped magnets or flexible sheets of Ferrite magnetic material, magnetized in an arrangement that is perpendicular to the application surface, for instance are typical. While there may be some room for manufacturing tolerances, it is believed that the tolerances generally may provide an angular difference from the magnetic axis of one magnet to another of approximately five degrees or less, as the desired angle relative to the applicator surface is to be normal.

It is believed that at least part of the therapeutic effect of magnetism on humans is the angle and strength at which the magnetic field and/or magnetic flux interacts with or encounters the nerve endings and/or blood vessels in a given area where applied. Since blood vessels and nerve endings are oriented at a wide variety of angles on both a two dimensional and on a three dimensional basis, it follows that a magnetic field or magnetic flux at varying or even random angles will maximize the therapeutic effect.

It is therefore an object of some embodiments of this invention to provide a magnetism applicator which provides application of magnetism such that the magnetic axis of the magnets is provided at varying and/or random angles relative to each other and/or relative to the application surface.

It is therefore an object of some embodiments of this invention to provide a system for making an arrangement of magnets in an applicator wherein the magnetic axis are at varying and/or random angles relative to one another and/or relative to the application surface.

Other objects, features, and advantages of this invention will appear from the specification, claims, and accompanying drawings which form a part hereof. In carrying out the objects of this invention, it is to be understood that its essential features are susceptible to change in design and structural arrangement, with only one practical, and preferred embodiment being illustrated in the accompanying drawings, as required.

BRIEF DESCRIPTION OF THE DRAWINGS

Preferred embodiments of the invention are described below with reference to the following accompanying drawings.

FIG. 13 is an elevation view of a string of magnets on a conductor wire after molding and after the alteration of the magnetic axis angles; and FIG. 14 is a perspective view of a string of magnets on a conductor wire as the string is rotated to alter the relative angles of the magnet axis of the magnets.

DETAILED DESCRIPTION OF THE PREFERRED EMBODIMENTS

Fasteners, materials, drive mechanisms, control circuitry, manufacturing and other means and components utilized to make and implement this invention are known and used in the field of the invention described, and their exact nature or type is not necessary for an understanding and use of the invention by a person skilled in the art or science; therefore, they will not be discussed in significant detail. Furthermore, the various components shown or described herein for any specific application of this invention can be varied or altered as anticipated by this invention and the practice of a specific application or embodiment of any element may already be widely known or used in the art or by persons skilled in the art or science; therefore, each will not be discussed in significant detail.

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

The terms magnet and magnetic material may include any type or kind of magnet or magnetic material with no one in particular being required to practice this invention. By way of providing some, but not an exhaustive list of examples, this may include without limitation, permanent magnets, magnetic materials which create a changing magnetic field, ferromagnetic components, and others. The magnets or magnetic material may be fluxing, fixed, moving or otherwise, within the contemplation of this invention, and may create pulsed, changing, fluxing, modulating, and/or fixed/constant magnetic, waved or energy fields (as a few examples) within the contemplation of this invention. They may including alternating poles, north poles, south poles, or combinations thereof, and different shapes of the magnets and magnetic fields, all within the same magnet or magnetic layer, within the contemplation of this invention.

The outer layer can be any type of material which is desirable for applying the magnetic field or for interfacing with the user, all within the contemplation of this invention.

Figure 1:
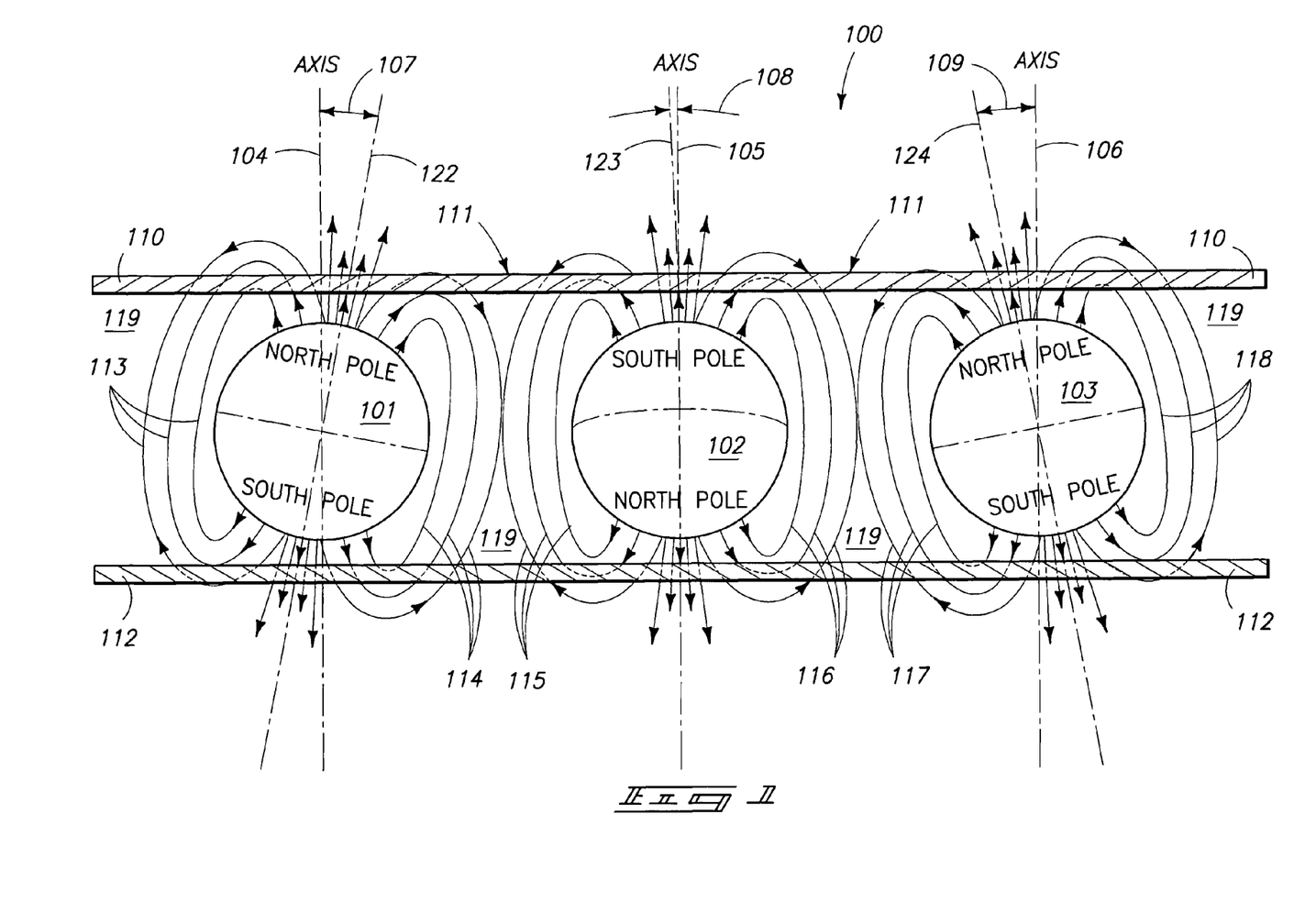
FIG. 1 is a schematic elevation view of one embodiment of this invention wherein the axis of the magnets are at random angles with respect to one another.

FIG. 1 is a schematic elevation view of one embodiment of this invention wherein the axis of the magnets are at random angles with respect to one another. FIG. 1 illustrates a magnetism application system 100, first magnet 101 with a magnetic axis 122 at angle 107 relative to a reference 104 normal or perpendicular to application surface 111, second magnet 102 with a magnetic axis 123 at angle 108 relative to a reference 105 normal or perpendicular to application surface 111, and third magnet 103 with a magnetic axis 123 at angle 109 relative to a reference 106 normal or perpendicular to application surface 111. Each magnet 101, 102 and 103 is shown held in place in applicator 119 with outer walls 110 and 112, with part of their respective magnetic fields 113, 114, 115, 116, 117 and 118 respectively, shown round said magnets 101, 102 and 103.

It will be appreciated by those of ordinary skill in the art that the magnetic flux created by a plurality of magnets with different angles will be multidirectional and will result in the application of a more desirable, improved and varied magnetic field.

Figure 2:
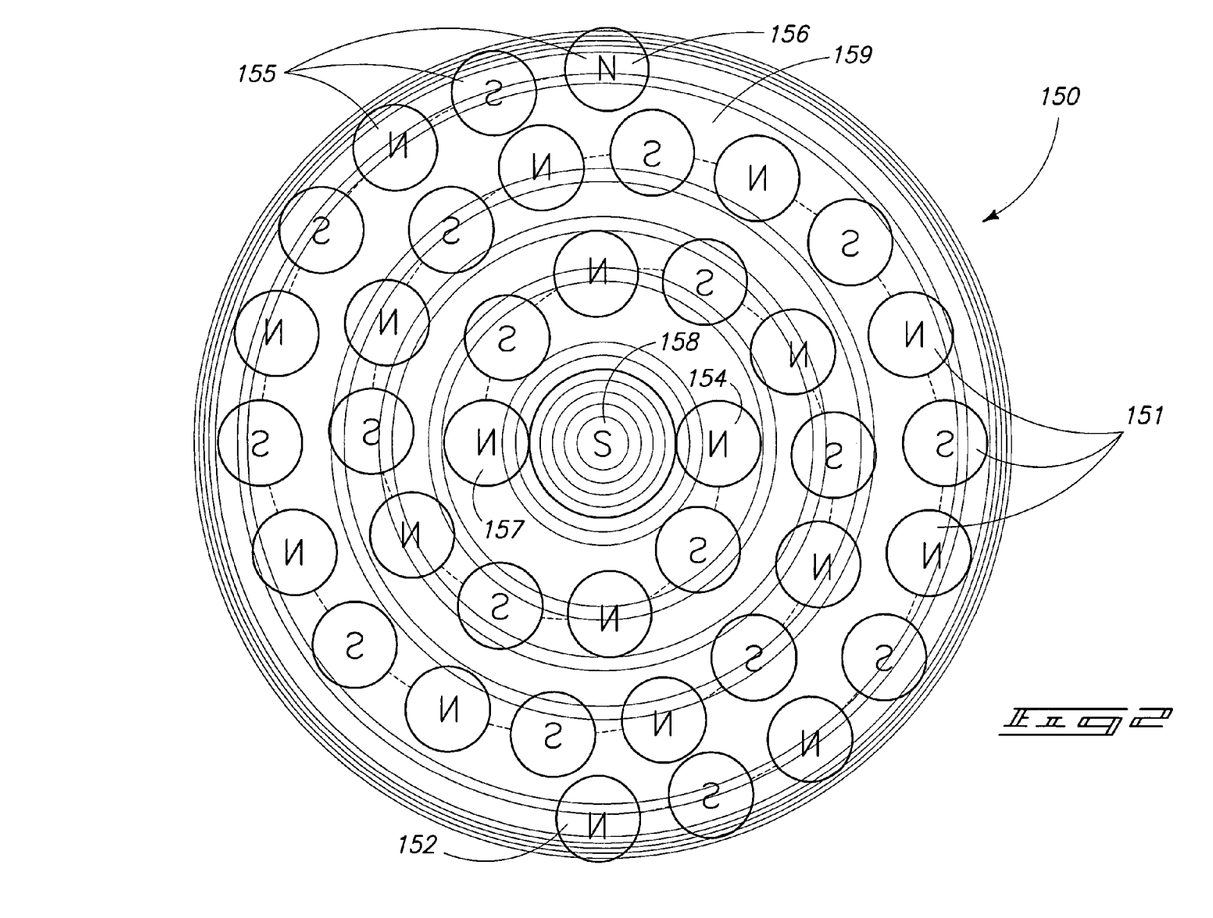
FIG. 2 is a top schematic view of one example of one embodiment of this invention wherein the magnets have been generally arranged around a center magnet.

FIG. 2 is a top schematic view of one example of one embodiment of this invention wherein the magnets have been generally arranged around a center magnet 158. The array 150 of magnets and polarity configuration is also shown by the respective references to the N north and S south poles of the magnets, with the magnets being held by an applicator base with an applicator base material. FIG. 2 shows an example of a configuration wherein two strings of spherical shaped magnets connected by a conductor have been configured around a center magnet 158. The first string includes magnets 155 with magnet 156 being the first outer magnet in the string and magnet 157 being the innermost magnet. The second string of magnets 151 is shown with magnet 152 being the first out magnet in the string and magnet 154 being the innermost magnet. The applicator base material may be any one of a number of different materials, with no one in particular being required to practice the invention, such as a flexible resin with silicon therein.

Figure 3:
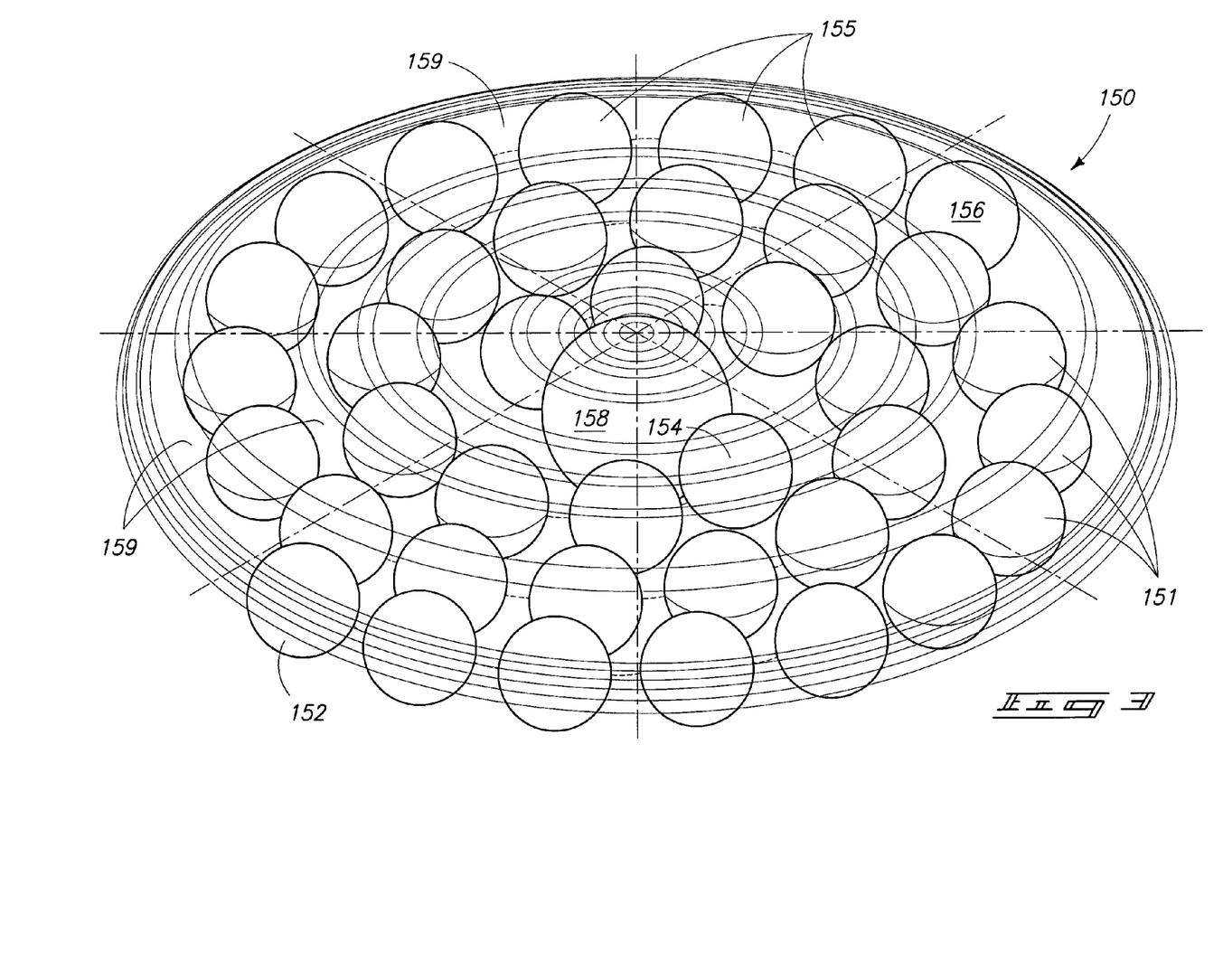
FIG. 3 is a perspective view of the embodiment illustrated in FIG. 2.

FIG. 3 is a perspective view of the embodiment illustrated in FIG. 2, and includes like numbered items to FIG. 2. FIG. 3 shows the configuration wherein two strings of spherical shaped magnets connected by a conductor, connector or string, have been configured around a center magnet 158. The first string includes magnets 155 with magnet 156 being the first outer magnet in the string and magnet 157 being the innermost magnet. The second string of magnets 151 is shown with magnet 152 being the first out magnet in the string and magnet 154 being the innermost magnet.

Figure 4:
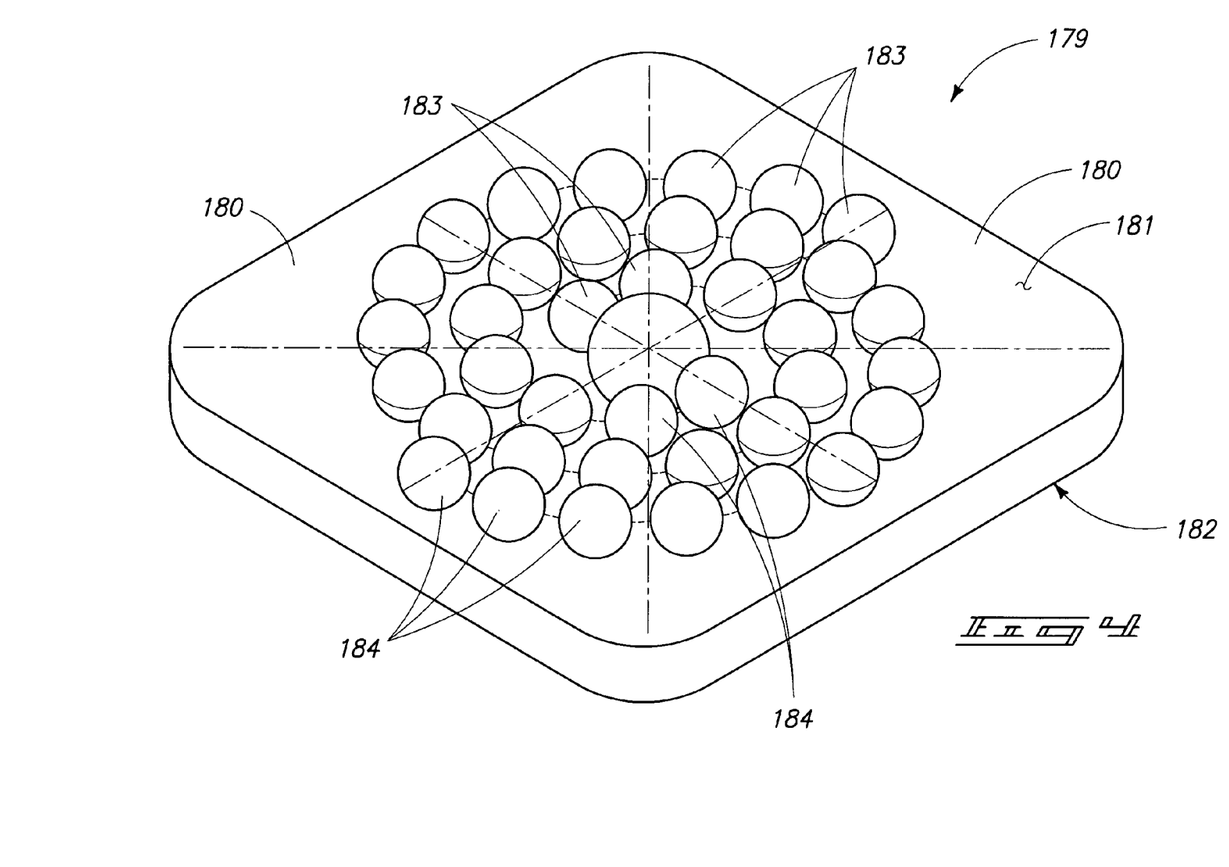
FIG. 4 is a perspective view of an embodiment of this invention with a magnet configuration in a flexible magnetic field applicator.

FIG. 4 is a perspective view of another one of the possible embodiments of this invention, with a magnet configuration in a flexible magnetic field applicator. FIG. 4 illustrates a magnet applicator 179 with applicator base 180 with applicator base top side 181 and applicator base bottom side 182. Within the applicator base 180 are a first string of magnets 183 and a second string of magnets 184.

Figures 5, 6:
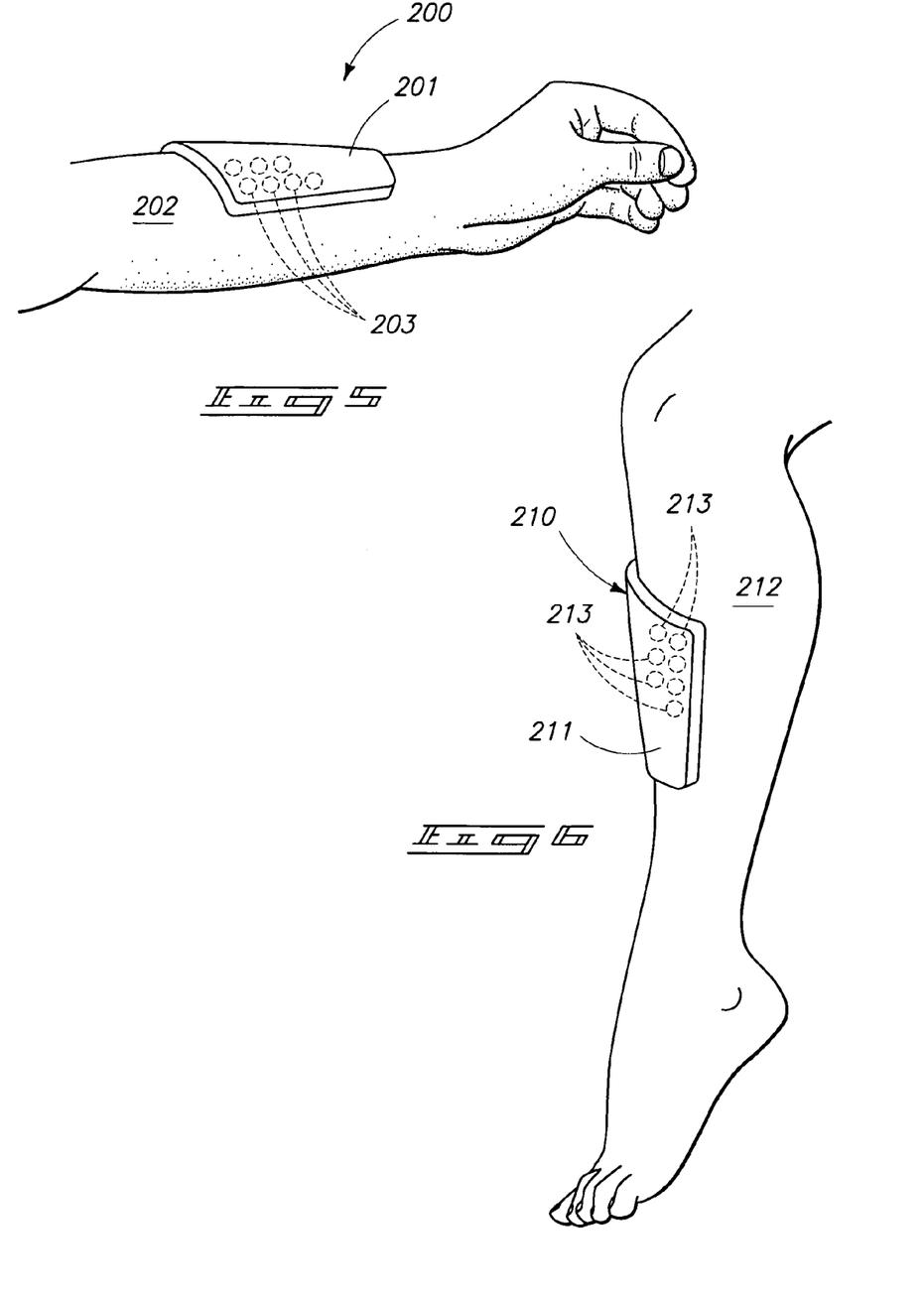
FIG. 5 is a perspective view of how one embodiment of this invention may be applied to an arm.
FIG. 6 is a perspective view of how one embodiment of this invention may be applied to a human leg.

FIG. 5 is a perspective view of how one embodiment of this invention 200 may be applied to an arm 202, showing applicator base 201 with magnets 203 shown therein. It will be appreciated by those of ordinary skill in the art that the strength and desired or actual therapeutic effect of the applicator system 200 may vary depending on the application, with no one in particular being required to practice the invention.

FIG. 6 is a perspective view of how one embodiment of an applicator system 210 contemplated by this invention may be applied to a human leg 212, showing applicator base 211 and magnets therein 213.

Figure 7:
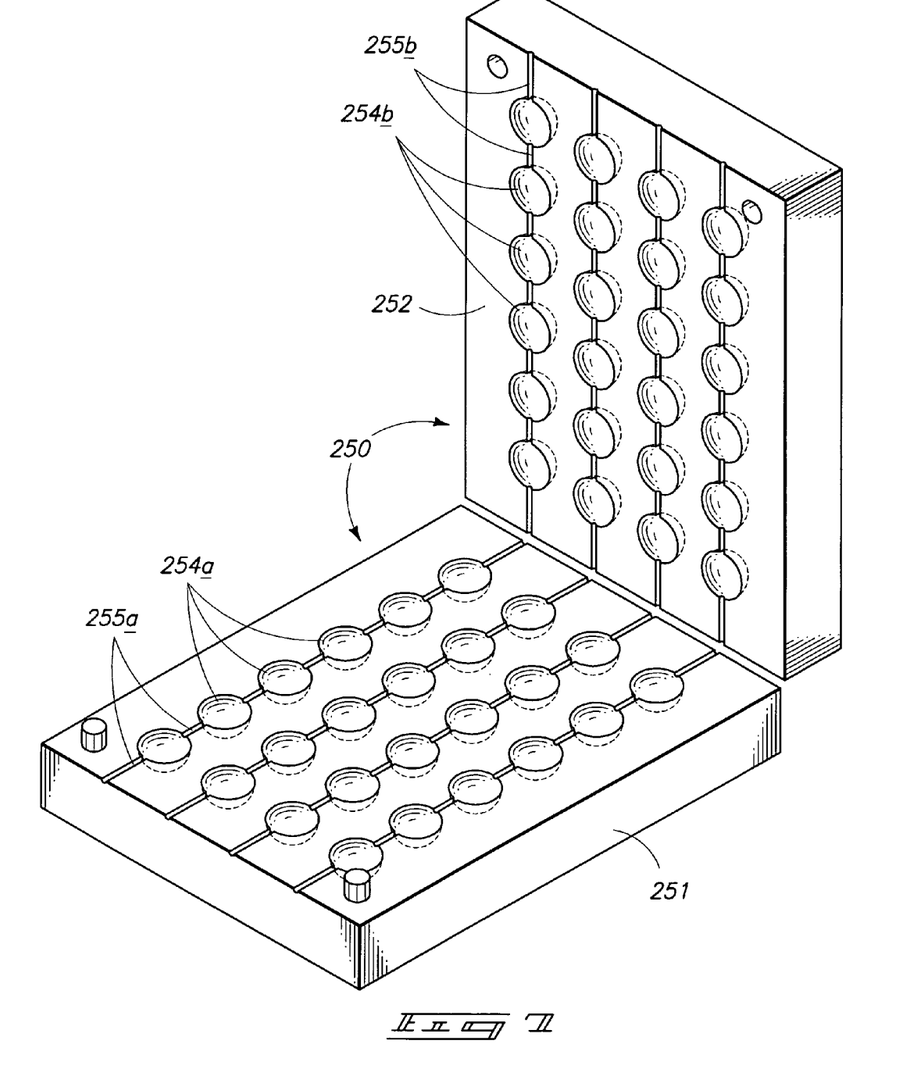
FIG. 7 is a perspective view of part of a mold configuration in which a string of magnets may be made for use in embodiments of this invention.

FIG. 7 is a perspective view of part of a mold configuration in which a string of magnets may be made for use in embodiments of this invention, illustrating mold 250 with a first half 251, second half 252, and a plurality of shaped apertures for receiving the material to be molded and a slot 255a for a conductor wire or other type of connector (such as a pliable connector) to be placed across each of the apertures in a string. For instance slot 255a and 255b would form the aperture to receive a conductor and mold apertures 254a and 254b together comprise the mold apertures to form or mold six spherical magnets all connected by a conductor or string.

Figure 8B:
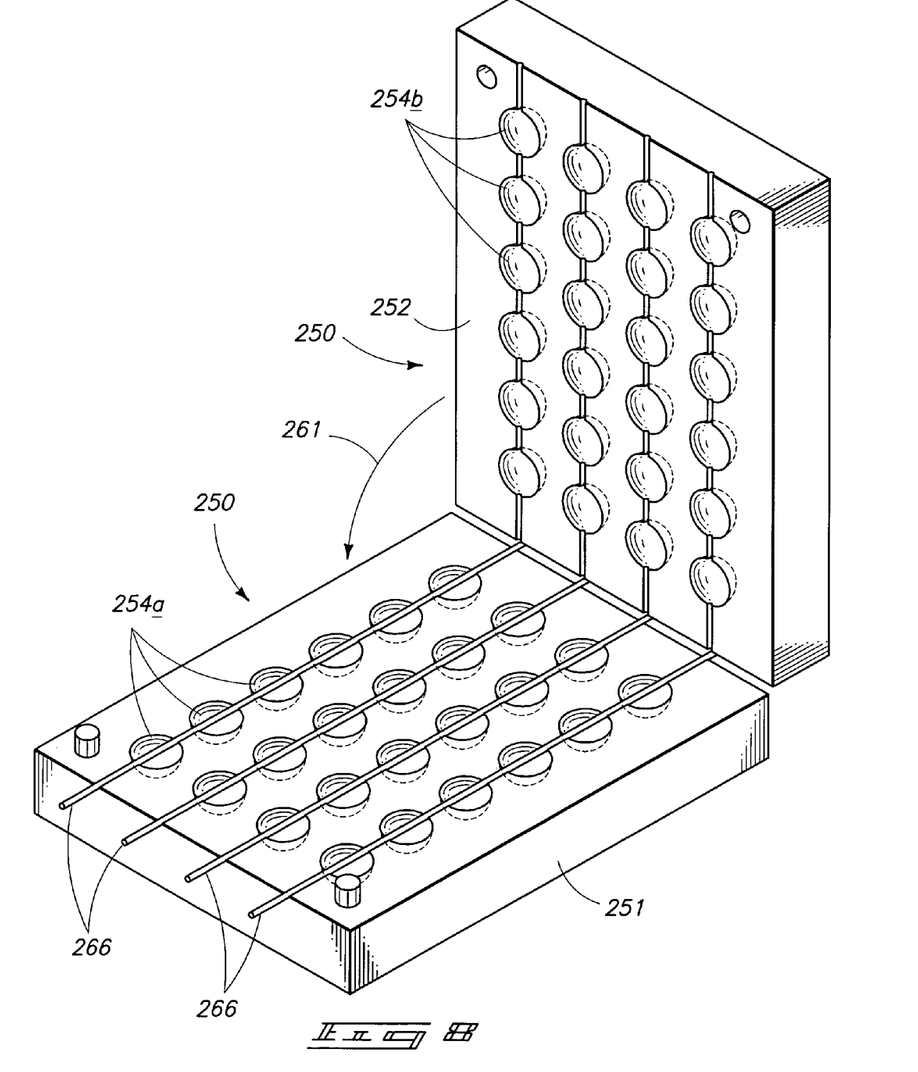
FIG. 8 is a perspective view of the mold shown in FIG. 7, wherein the conductor wire or connector has been inserted therein before molding the magnets.

FIG. 8 is a perspective view of the mold shown in FIG. 7, wherein the conductor wire has been inserted therein before molding the magnets. FIG. 8 shows the mold 250 with the conductor 266 placed in the slot 255a from FIG. 7 and just prior to molding. Arrow 261 indicates that the two mold sections 251 and 252 will be moved together, with no particular way of doing so be required to practice this invention.

Figure 9:
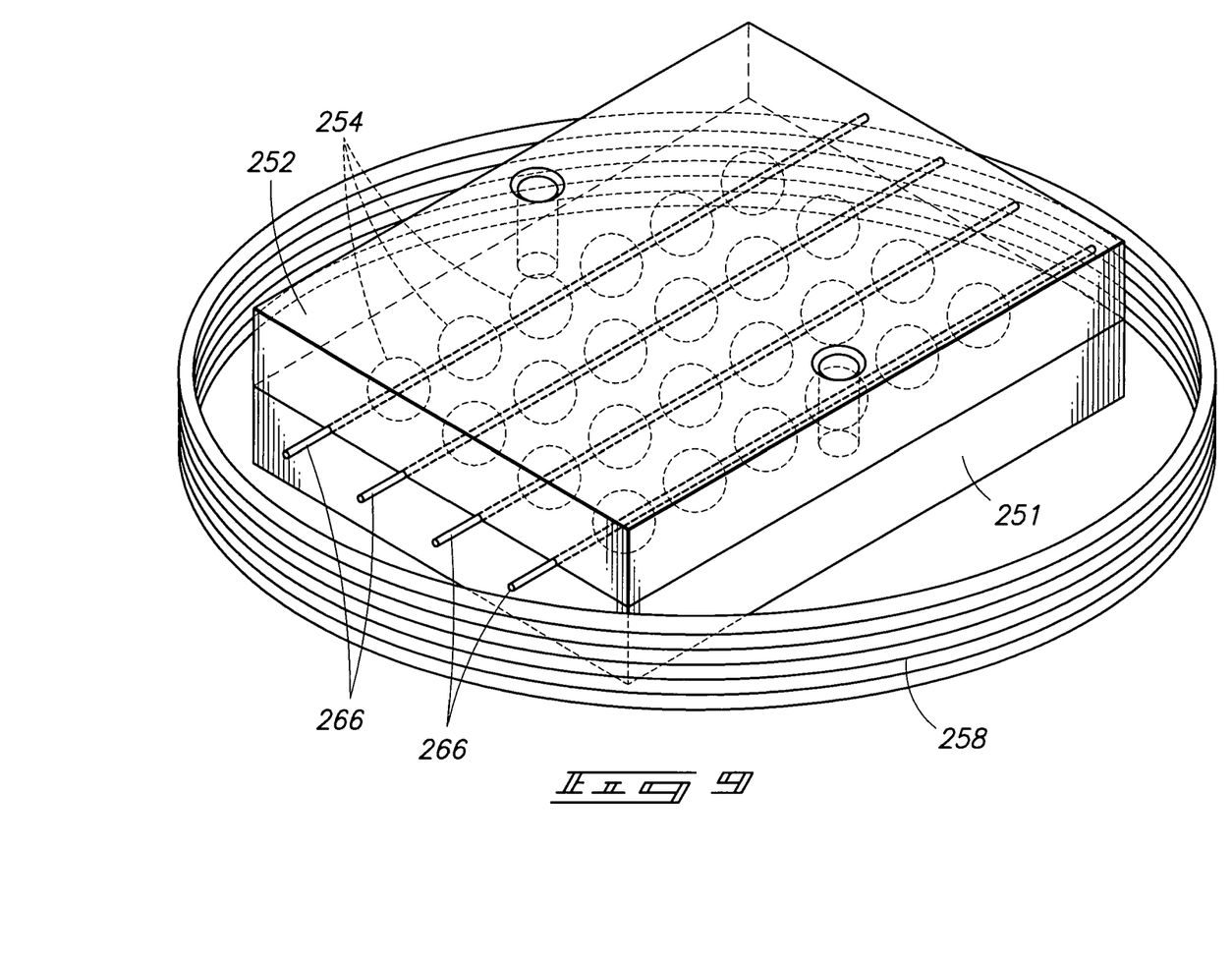
FIG. 9 is a perspective schematic view of the mold shown in FIG. 7, with an electrical coil around the mold, used in molding the magnets.

FIG. 9 is a perspective schematic view of the mold shown in FIG. 7, schematically showing an electrical coil 258 around the mold parts 251 and 252. Although there are different ways and procedures to mold magnets, in this case a mixture of any one of a number of magnetic materials may be inserted or injected into the mold cavities 254 (spherically shaped in this example), possibly mixed with another material such as a nylon or nylon pellets. The combination of the magnetic material (ferrite as an example) and the nylon will have a random or magnetic domain; however during the molding process the coil 258 will receive electrical current and cause the polarity to align. In that process the mold becomes a magnet and causes the material in the mold cavities to also become magnets with a conductor there-through. The mold is generally heated up to approximately six hundred degrees Fahrenheit during the molding process.

An alternative way to impose varying or different magnetic axis on a plurality of magnets in a string of magnets would be to place small permanent magnets (high temperature magnets) around each individual magnet cavity within the mold at the desired angles, which would then align the poles of each magnet produced therein.

Figures 10, 11:
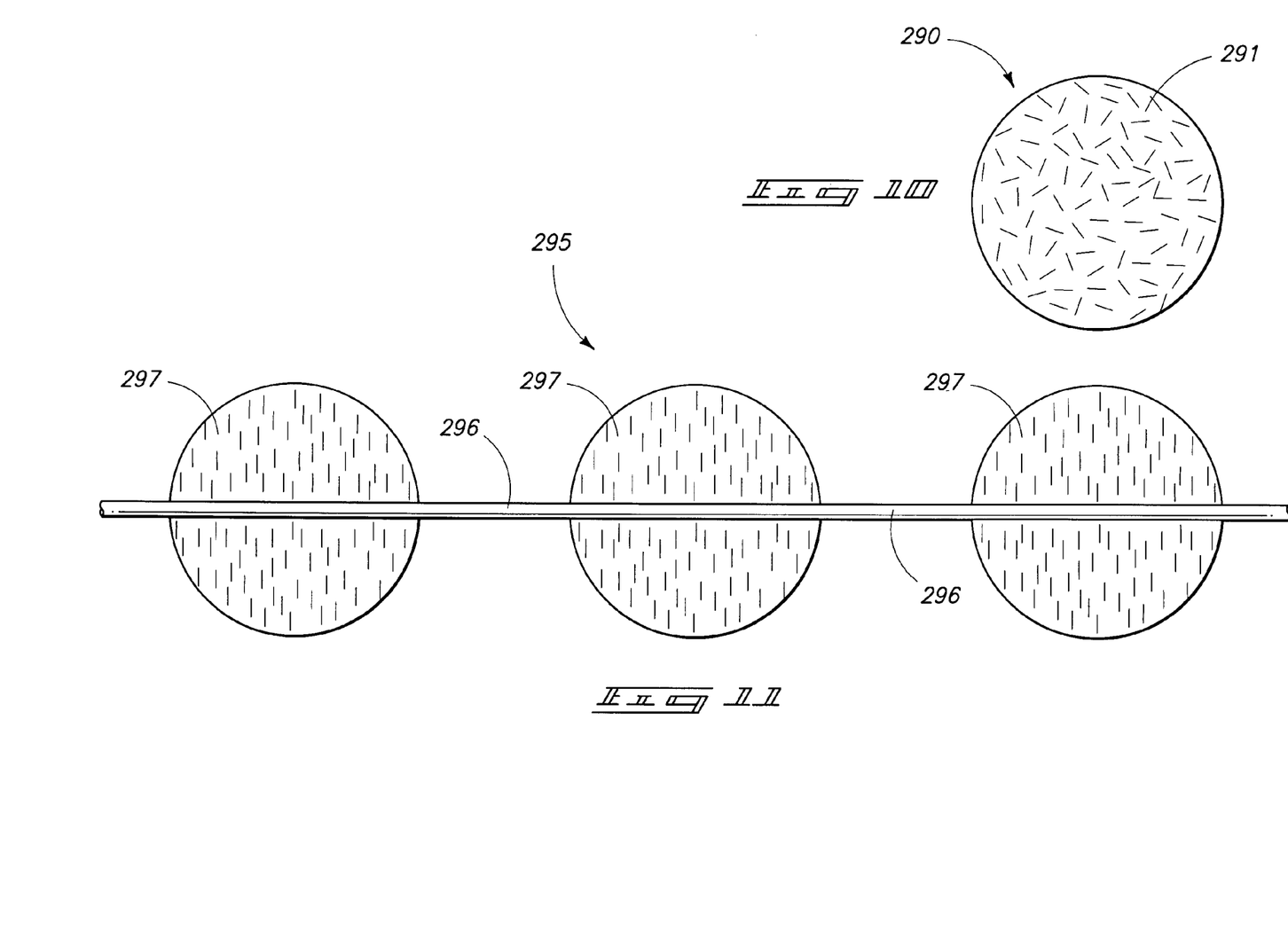
FIG. 10 is a elevation schematic view of a spherically shaped composition that will become a magnet during the molding process.
FIG. 11 is an elevation view of a plurality of magnets on a conductor wire or connector after molding and magnetization, showing the alignment of the composition.
Figure 11:
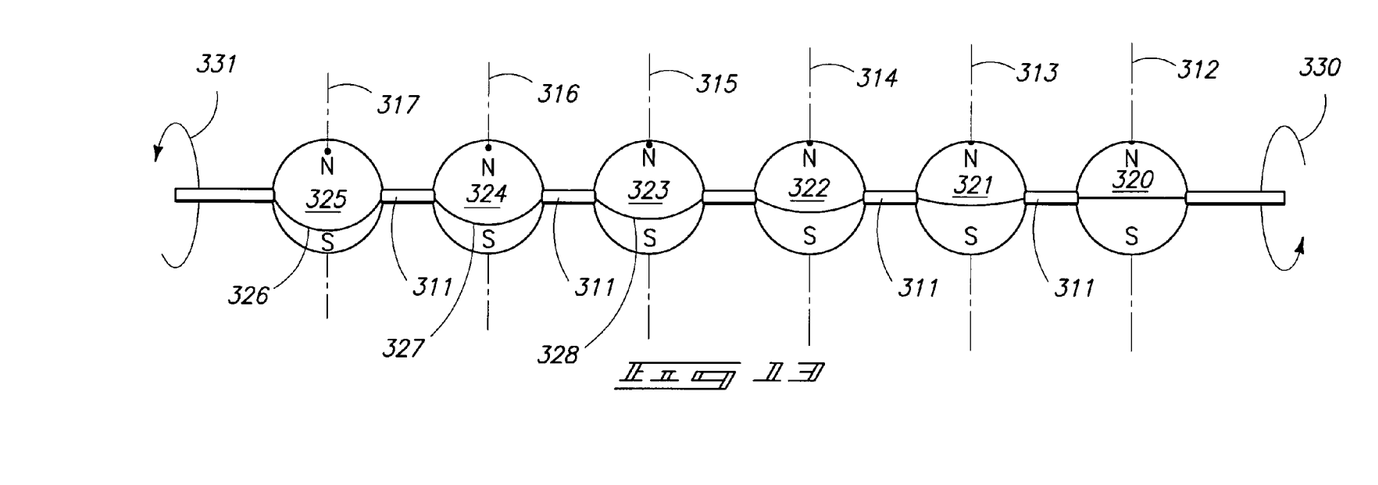

FIG. 10 is a elevation schematic view of a spherically shaped composition 290 that will become a magnet during the molding process, and may schematically represent the nylon and magnetic material (ferrite) mixture injected into the mold. Before molding a random pattern 291 is shown in FIG. 10. It will also be appreciated by those of ordinary skill in the art that this invention is not limited to any one particular type of magnetic material such as ferrite, or to any particular type of other material such as nylon, but any one of a number of different materials may be used within the contemplation of this invention.

FIG. 11 is an elevation view of a string 295 or plurality of magnets 297 on a conductor wire 296 (which may for instance be comprised of copper), after molding and magnetization, showing the alignment of the composition. FIG. 11 illustrates how the material or magnetic polarity of the material becomes aligned during the molding process as a result of the use of the coil.

Figure 12:
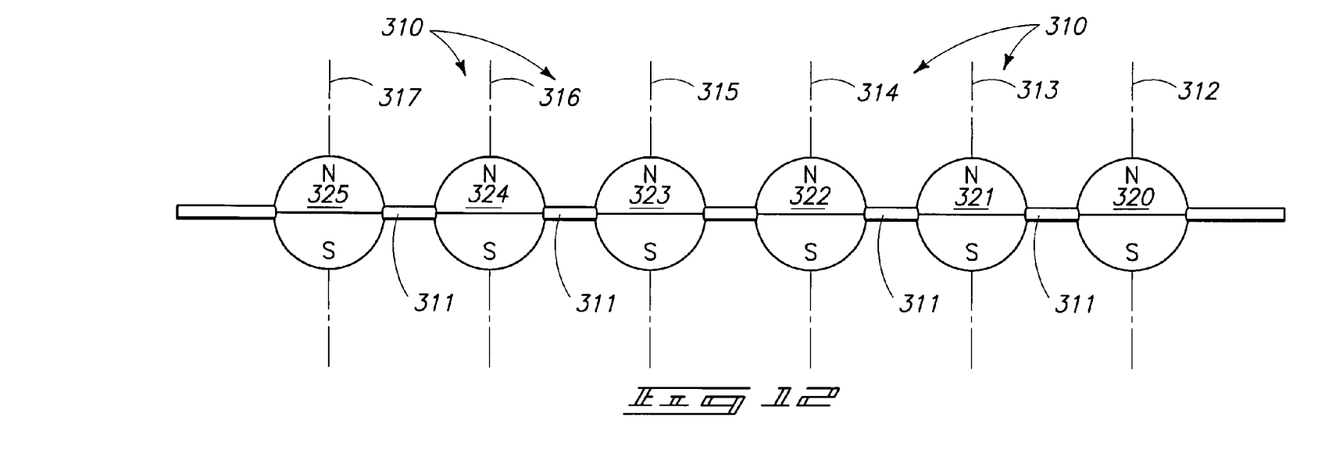
FIG. 12 is an elevation view of a string of magnets on a conductor wire after molding and before the alteration of the magnetic axis angles and encapsulation.

FIG. 12 is an elevation view of a string 310 of magnets 320, 321, 322, 323, 324 and 325, on a conductor wire 311 after molding and with the north and south magnetic poles, or the axis 312, 313, 314, 315, 316, and 317, being generally aligned.

FIG. 13 is an elevation view of the string 310 of magnets as one end of the string 310 is twisted with respect to the other end, as represented by arrows 330 and 331. The twisting of the conductor 311 randomly alters the angle of the magnetic axis 312-317 with respect to one another, as shown representatively by the schematic and exemplary dividing lines 326, 327, 328 on some of the magnets shown.

FIG. 14 is a perspective view of the string 310 of magnets 320-325 on the conductor wire, and illustrates the random and varying relative angles of the magnetic axis 312-317, as one end of the string 310 has been rotated with respect to the other end of the string 310 of magnets. FIG. 14 for instance shows magnets 324 and 325 at substantial angles relative to other magnets on the string of magnets, greater for instance that thirty, forty five and sixty degrees.

The connector between magnets may be a conductor or any other type of material, depending on the specific embodiment or aspect of the invention, with no one in particular being required to practice the invention. For instance if copper is utilized, each magnet may be rotated whatever specific angle desired with respect to the adjacent magnet of the plurality of magnets or relative to any other magnet on the string of magnets, or they may be rotated to achieve random angles of the magnetic axis of each of the plurality of magnets.

It will be appreciated by those of ordinary skill in the art that the use of a conductor such as copper, will allow the magnetic axis of the magnets on the string to be rotated to random angles, or if desired, to pre-determined or specific angles relative to others within the plurality of magnets.

As will be appreciated by those of reasonable skill in the art, there are numerous embodiments to this invention, and variations of elements and components which may be used, all within the scope of this invention.

In one embodiment for example a magnetic field applicator system is provided, comprising: an applicator base; a plurality of magnets in the applicator base, each the plurality of magnets having a magnetic axis at an angle different to other magnets in the plurality of magnets.

Additional and/or other embodiments of that in the preceding paragraph may be: further wherein the magnet medium includes silicon; further wherein the magnetic axis of each of the plurality of magnets is random relative to the magnetic axis of other in the plurality of magnets; further wherein the plurality of magnets are connected by a connector (which may be copper); further wherein the plurality of magnets are fixed into the magnet medium in a generally arcuate pattern around a center; further wherein the magnetic axis of each of the plurality of magnets is randomly different to other magnets in the plurality of magnets; and/or wherein the plurality of magnets are each shaped as a sphere.

It will also be appreciated by those of ordinary skill in the art that the angle of the magnetic axis of each the plurality of magnets to other magnets in the plurality of magnets is at least five degrees, fifteen, twenty five, forty-five or sixty degrees.

In another embodiment, a method embodiment, a method of making a magnetic field applicator system may be provided with a plurality of magnets each with a magnet axis different to the magnetic axis of others of the plurality of magnets, comprising: providing a mold with a plurality of magnet cavities; positioning a connector between each of the plurality of magnet cavities in the mold; molding a plurality of magnets in the plurality of magnet cavities in the mold such that the plurality of magnets are attached to one another by the connector and further such that each of the plurality of magnets has a magnetic axis which is generally aligned with other magnets in the plurality; rotating a first end of the plurality of magnets relative to a second end of the plurality of magnets such that the magnetic axis of the plurality of magnets are no longer generally aligned; and/or encapsulating the plurality of magnets into a magnet medium such that the magnetic axis of the plurality of magnets are not generally aligned.

There may be additional and/or other embodiments or aspects to the method described in the preceding paragraph, such as a method: further wherein the magnetic axis of each of the plurality of magnets is random relative to the magnetic axis of other in the plurality of magnets; wherein the connector is a copper wire; further wherein the magnet medium includes silicon; further wherein the plurality of magnets are fixed into the magnet medium in a generally arcuate pattern around a center; further wherein the magnet axis of the plurality of magnets are random with respect to others of the plurality of magnets; and or further wherein rotating the first end of the plurality of magnets relative to the second end of the plurality of magnets results in the angle of the magnetic axis of each the plurality of magnets to other magnets in the plurality of magnets being at least five, fifteen, thirty, forty-five and sixty degrees.

In yet another embodiment, a magnetic field applicator system is provided which comprises: a string including a plurality of individual magnets, each of the plurality of individual magnets spaced apart from and connected to another one of the plurality of individual magnets by a pliable connector; wherein each the plurality of individual magnets having a magnetic axis; and further wherein the pliable connector is configured such that each of the plurality of individual magnets may be rotated with respect an adjacent individual magnet on the string to a desired relative position.

Further and/or alternate aspects of the embodiment described in the preceding paragraph, may further include a system wherein each of the plurality of individual magnets are spherical shaped; and/or further rotation of each of the plurality of individual magnets with respect to an adjacent individual magnet creates a pre-determined or desired angle between the magnetic axis of each of the respective individual magnets.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A magnetic field applicator system comprising:
   a flexible applicator base;
   a plurality of magnets embedded and fixed within the applicator base such that each of the plurality of magnets is embedded within the applicator base with its magnetic axis at an angle different to some of the other magnets in the plurality of magnets when the applicator base is approximately planar;
   wherein the plurality of magnets as embedded within the applicator base are configured to each create magnetic fields external to the applicator base at different angles; and
   further wherein the angle of the magnetic axis of each the plurality of magnets relative to other magnets in the plurality of magnets is at least five degrees.

2. A magnetic field applicator system as recited in claim 1, and further wherein the applicator base includes silicon.

3. A magnetic field applicator system as recited in claim 1, and further wherein the magnetic axis of each of the plurality of magnets is random relative to the magnetic axis of others in the plurality of magnets.

4. A magnetic field applicator system as recited in claim 1, and further wherein the plurality of magnets are connected by a connector.

5. A magnetic field applicator system as recited in claim 4, and further wherein the connector is a copper wire.

6. A magnetic field applicator system as recited in claim 1, and further wherein the plurality of magnets are fixed into the applicator base in a generally arcuate pattern wrapped around a center and with adjacent magnets in the plurality of magnets having respective north and south poles in generally opposite directions from north and south poles of adjacent magnets in the plurality of magnets.

7. A magnetic field applicator system as recited in claim 1, and further wherein the magnetic axis of each of the plurality of magnets is randomly different to other magnets in the plurality of magnets.

8. A magnetic field applicator system as recited in claim 1, and further wherein the plurality of magnets are each shaped as a sphere.

9. A magnetic field applicator system as recited in claim 1, and further wherein the angle of the magnetic axis of each the plurality of magnets relative to other magnets in the plurality of magnets is at least five degrees.

10. A magnetic field applicator system as recited in claim 1, and further wherein the angle of the magnetic axis of each the plurality of magnets relative to other magnets in the plurality of magnets is at least fifteen degrees.

11. A magnetic field applicator system as recited in claim 1, and further wherein the angle of the magnetic axis of each the plurality of magnets relative to other magnets in the plurality of magnets is at least twenty five degrees.

12. A magnetic field applicator system as recited in claim 1, and further wherein the angle of the magnetic axis of each the plurality of magnets relative to other magnets in the plurality of magnets is at least forty five degrees.

13. A magnetic field applicator system as recited in claim 1, and further wherein the angle of the magnetic axis of each the plurality of magnets relative to other magnets in the plurality of magnets is at least sixty degrees.

14. A magnetic field applicator system as recited in claim 1, and further comprising
   an application surface on the applicator base;
   a first magnet in the plurality with a north magnetic pole and a south magnetic pole;
   a second magnet in the plurality adjacent the first magnet, the second magnet having a north magnetic pole and a south magnetic pole;
   a third magnet in the plurality adjacent the second magnet, the third magnet having a north magnetic pole and a south magnetic pole;
   wherein the north pole of the first magnet is generally oriented toward the application surface, the south pole of the second magnet is generally oriented toward the application surface, and the north pole of the third magnet is generally oriented toward the application surface.

15. A magnetic field applicator system as recited in claim 14, and further wherein the applicator base is flexible to better configure to interact with a user.

16. A magnetic field applicator system as recited in claim 15, and further wherein the first magnet, second magnet and third magnet are configured to create magnetic flux external to the applicator base at different angles.

17. A magnetic field applicator system as recited in claim 15, and further wherein the plurality of magnets are configured to create a non-uniform magnetic flux external to the applicator base.

18. A magnetic field applicator system as recited in claim 15, and further wherein the non-uniform magnetic flux external to the applicator base produces a therapeutic effect on a user within the magnetic flux created external to the applicator base.

19. A magnetic field applicator system comprising:
   a string including a plurality of magnets, each of the plurality of individual magnets spaced apart from and connected to another one of the plurality of individual magnets by a pliable connector;
   wherein each of the plurality of magnets have a magnetic axis and create a surrounding magnetic field, and further wherein the magnetic axes of each of the plurality of magnets on the string are initially generally aligned; and
   further wherein the string is embedded in an applicator base while in a twisted orientation such that the magnetic axes of each of the plurality of magnets are at an angle different from other magnets in the plurality of magnets.

20. A magnetic field applicator system as recited in claim 19, and further wherein each of the plurality of individual magnets are spherically shaped.

21. A magnetic field applicator system as recited in claim 20, and further wherein rotation of each of the plurality of individual magnets with respect to an adjacent individual magnet creates an angle between a magnetic axis of each of the respective individual magnets and resulting magnetic flux.

22. A magnetic field applicator system as recited in claim 19, and further wherein the applicator base is flexible to better configure to interact with a user of the applicator system.

23. A magnetic field applicator system comprising:
   a flexible applicator base;
   a plurality of magnets embedded and fixed within the applicator base such that each of the plurality of magnets is embedded within the applicator base with its magnetic axis at a random angle relative to the applicator base and to other magnets in the plurality of magnets of at least five degrees difference when the applicator base is approximately planar;
   wherein the plurality of magnets as embedded within the applicator base are configured to each create magnetic fields external to the applicator.

24. A magnetic field applicator system comprising:
a plurality of individual magnets spaced apart from one another along a string;
wherein each of the plurality of magnets have a magnetic axis and create a surrounding magnetic field, and further wherein the magnetic axis of each of the plurality of magnets on the string are initially generally aligned; and
further wherein the plurality of individual magnets are placed in randomly angled orientation relative to one another and then embedded in an applicator base such that the magnetic axes of each of the plurality of magnets are at an angle different from other magnets in the plurality of magnets.

25. A magnetic field applicator system as recited in claim 24, and further wherein the magnetic axis of each of the plurality of magnets are randomly set at angles different from other magnets in the plurality of magnets.

\* \* \* \* \*